(12) United States Patent
Kato et al.

(10) Patent No.: US 11,180,457 B2
(45) Date of Patent: Nov. 23, 2021

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventors: Tsuyoshi Kato, Ichihara (JP); Daisuke Yagyu, Ichihara (JP); Naoya Fukumoto, Ichihara (JP); Yuta Yamaguchi, Kawasaki (JP); Masumi Kuritani, Tokyo (JP); Katsumi Murofushi, Ichihara (JP); Masaki Nanko, Ichihara (JP); Hiroyuki Tomita, Ichihara (JP)

(73) Assignee: SHOWA DENKO K. K., Tokyo (JP)

( * ) Notice: Subject to any disclaimer, the term of this patent is extended or adjusted under 35 U.S.C. 154(b) by 0 days.

(21) Appl. No.: 16/759,515

(22) PCT Filed: Aug. 28, 2018

(86) PCT No.: PCT/JP2018/031788
§ 371 (c)(1),
(2) Date: Apr. 27, 2020

(87) PCT Pub. No.: WO2019/087548
PCT Pub. Date: May 9, 2019

(65) Prior Publication Data
US 2020/0283392 A1    Sep. 10, 2020

(30) Foreign Application Priority Data

Oct. 31, 2017 (JP) .............................. JP2017-210678

(51) Int. Cl.
*C07D 231/12* (2006.01)
*C07D 277/24* (2006.01)
(Continued)

(52) U.S. Cl.
CPC ......... *C07D 231/12* (2013.01); *C07D 277/24* (2013.01); *C07D 333/16* (2013.01);
(Continued)

(58) Field of Classification Search
CPC .......... C10N 2030/06; C10N 2050/025; C10N 2040/14; C10N 2040/18; C10N 2050/023;
(Continued)

(56) References Cited

U.S. PATENT DOCUMENTS 4,526,833 A * 7/1985 Burguette ............ C09D 171/02
428/336
2015/0371671 A1  12/2015 Inoue
(Continued)

FOREIGN PATENT DOCUMENTS

JP    10-143838 A    5/1998
JP    2866622 B      3/1999
(Continued)

OTHER PUBLICATIONS

International Search Report for PCT/JP2018/031788 dated Nov. 20, 2018.

*Primary Examiner* — Vishal V Vasisth
(74) *Attorney, Agent, or Firm* — Sughrue Mion, PLLC

(57) ABSTRACT

Provided is a fluorine-containing ether compound capable of forming a lubricant layer having excellent wear resistance even when the thickness is thin, and suitable as a material of a lubricant for a magnetic recording medium. The fluorine-containing ether compound is a compound represented by the following formula (1): $R^1\text{—}R^2\text{—}CH_2\text{—}R^3\text{—}CH_2\text{—}R^4\text{—}R^5$; wherein $R^3$ is a perfluoropolyether chain; $R^1$ is a terminal group bonded to $R^2$; $R^5$ is a terminal group bonded to $R^4$; $R^1$ is an alkenyl group or an alkynyl group; $R^5$ is a group containing a heterocyclic ring; $R^2$ is represented by (Continued)

the following formula (2); $R^4$ is represented by the following formula (3); and a in the formula (2) and b in the formula (3) are each independently an integer of 1 to 3.

[Chemical 1]

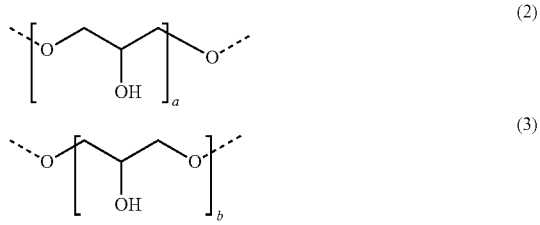

10 Claims, 1 Drawing Sheet

(51) Int. Cl.
*C07D 333/16* (2006.01)
*C10M 107/24* (2006.01)
*C10M 107/38* (2006.01)
*C10M 107/40* (2006.01)
*C10M 107/46* (2006.01)
*G11B 5/725* (2006.01)

(52) U.S. Cl.
CPC ........ *C10M 107/24* (2013.01); *C10M 107/38* (2013.01); *C10M 107/40* (2013.01); *C10M 107/46* (2013.01); *G11B 5/725* (2013.01); *C10M 2213/0606* (2013.01)

(58) Field of Classification Search
CPC .............. C10M 147/00; C10M 107/38; C10M 107/24; C10M 107/40; C10M 107/46; C10M 2221/04; C10M 2217/06; C10M 2213/043; C10M 2213/04; C10M 2209/10; C10M 2213/0606; C08G 65/331; G11B 5/7257; G11B 5/7266; G11B 5/725; C07D 231/12; C07D 333/16; C07D 277/24
See application file for complete search history.

(56) References Cited

U.S. PATENT DOCUMENTS

2016/0068778 A1   3/2016  Conley et al.
2017/0260472 A1   9/2017  Sagata et al.

FOREIGN PATENT DOCUMENTS

| JP | H1160720 A | * | 3/1999 |
| JP | 2009-211765 A | | 9/2009 |
| JP | 2012-033253 A | | 2/2012 |
| WO | 2015/087596 A1 | | 6/2015 |
| WO | 2016/084781 A1 | | 6/2016 |
| WO | 2017/145995 A1 | | 8/2017 |
| WO | 2017/154403 A1 | | 9/2017 |

* cited by examiner

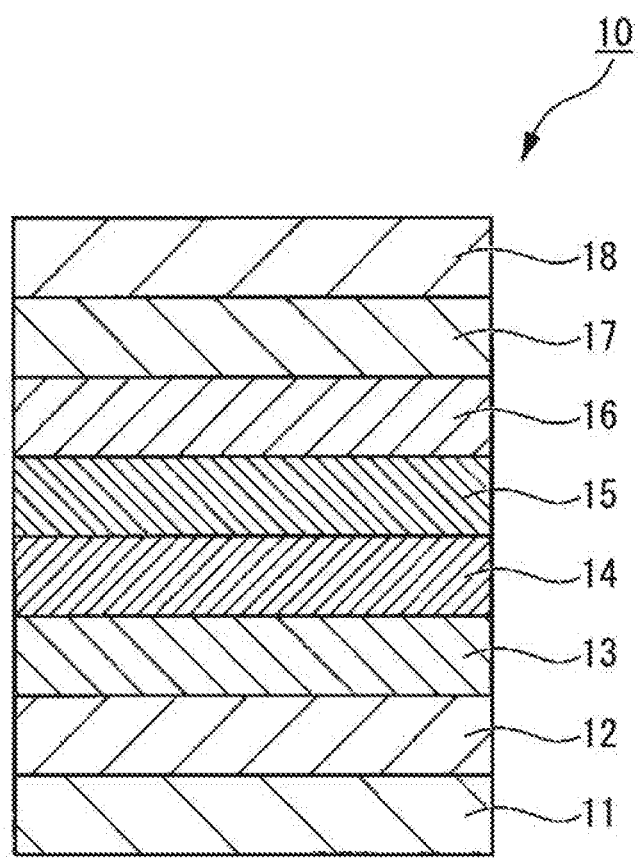

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATIONS

This application is a National Stage of International Application No. PCT/JP2018/031788 filed Aug. 28, 2018, claiming priority based on Japanese Patent Application No. 2017-210678 filed Oct. 31, 2017.

BACKGROUND OF THE INVENTION

Field of the Invention

The present invention relates to a fluorine-containing ether compound suitable for use as a lubricant for a magnetic recording medium, a lubricant for a magnetic recording medium containing the same, and a magnetic recording medium.

Background

In order to improve the recording density of a magnetic recording/reproducing apparatus, a magnetic recording medium suitable for a high recording density has been developed.

Conventionally, a magnetic recording medium has a recording layer formed on a substrate and a protective layer such as a carbon layer formed on the recording layer. The protective layer protects the information recorded in the recording layer and improves the slidability of a magnetic head. However, the durability of the magnetic recording medium cannot be sufficiently obtained only by providing the protective layer on the recording layer. For this reason, a lubricant is generally applied to the surface of the protective layer to form a lubricant layer.

As a lubricant used in forming a lubricant layer of a magnetic recording medium, for example, a lubricant containing a fluorine-based polymer having a repeating structure containing $CF_2$ has been proposed (For example, see Patent Documents 1 to 2.).

For example, Patent Document 1 discloses a perfluoropolyether derivative having a heterocyclic ring at a terminal. Further, Patent Document 2 discloses a fluorine-containing compound in which a fluoroalkyl group and an alkenyl group are linked by an alkylene group having a polar group.

Patent Document

[Patent Document 1] Japanese Unexamined Patent Application, First Publication No. 2012-33253
[Patent Document 2] Japanese Patent No. 2866622

SUMMARY OF THE INVENTION

In the magnetic recording/reproducing apparatus, it is required to further reduce the flying height of the magnetic head. Therefore, it is required to further reduce the thickness of the lubricant layer in the magnetic recording medium.

However, generally, when the thickness of the lubricant layer is reduced, the coverage rate of the lubricant layer is lowered, and the wear resistance of the magnetic recording medium tends to be lowered.

The present invention has been made in view of the above circumstances, and it is an object of the present invention to provide a fluorine-containing ether compound which can form a lubricant layer having excellent wear resistance even when the thickness is small and can be suitably used as a material of a lubricant for a magnetic recording medium.

Another object of the present invention is to provide a lubricant for a magnetic recording medium containing the fluorine-containing ether compound of the present invention.

Another object of the present invention is to provide a magnetic recording medium which has a lubricant layer containing the fluorine-containing ether compound of the present invention and has excellent reliability and durability.

The present inventors have conducted extensive research to solve the above problems.

As a result, it has been found that a fluorine-containing ether compound may be obtained by arranging linkage groups having a specific structure between a perfluoropolyether chain and a first terminal group of a molecule and between the perfluoropolyether chain and a second terminal group, respectively, wherein the linkage groups having a specific structure are linkage groups having an ether bond (—O—), a methylene group (—$CH_2$—), and a methylene group in which one hydrogen atom is substituted by a hydroxyl group (—CH(OH)—); the first terminal group is an alkenyl group or an alkynyl group; and the second terminal group is a group containing a heterocyclic ring. And then, the present invention has been conceived.

That is, the present invention relates to the following matters.

[1] A fluorine-containing ether compound represented by the following formula (1), $$R^1—R^2—CH_2—R^3—CH_2—R^4—R^5 \qquad (1)$$

wherein, in the formula (1), $R^3$ is a perfluoropolyether chain; $R^1$ is a terminal group bonded to $R^2$; $R^5$ is a terminal group bonded to $R^4$; $R^1$ is an alkenyl group or an alkynyl group; $R^5$ is a group containing a heterocyclic ring; $R^2$ is represented by the following formula (2); $R^4$ is represented by the following formula (3); and a in the formula (2) and b in the formula (3) are each independently an integer of 1 to 3.

[Chemical 1]

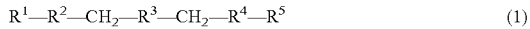

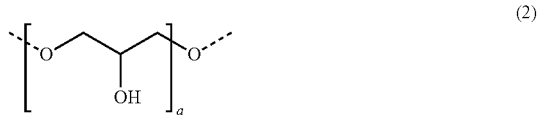

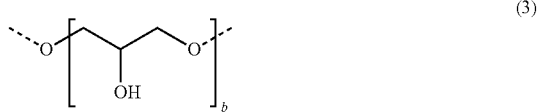

[2] The fluorine-containing ether compound according to [1], wherein $R^1$ in the formula (1) is an alkenyl group having 2 to 8 carbon atoms or an alkynyl group having 3 to 8 carbon atoms.

[3] The fluorine-containing ether compound according to [1], wherein $R^1$ in the formula (1) is at least one selected from the group consisting of an allyl group, a butenyl group, a pentenyl group and a propargyl group.

[4] The fluorine-containing ether compound according to any one of [1] to [3], wherein $R^5$ in the formula (1) is at least one selected from the group consisting of a group containing a thiophene ring, a group containing a thiazole ring, and a group containing a pyrazole ring.

[5] The fluorine-containing ether compound according to any one of [1] to [4], wherein $R^3$ in the formula (1) is any one of the following formulae (4) to (6),

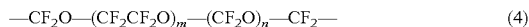

$$-CF_2O-(CF_2CF_2O)_m-(CF_2O)_n-CF_2- \quad (4)$$

wherein, in the formula (4), m and n represent an average degree of polymerization and each of them represents 0 to 30, and m or n is 0.1 or more.

$$-CF(CF_3)-(OCF(CF_3)CF_2)_y-OCF(CF_3)- \quad (5)$$

wherein, in the formula (5), y represents an average degree of polymerization and represents 0.1 to 30.

$$-CF_2CF_2O-(CF_2CF_2CF_2O)_z-CF_2CF_2- \quad (6)$$

wherein, in the formula (6), z represents an average degree of polymerization and represents 0.1 to 30.

[6] The fluorine-containing ether compound according to any one of [1] to [5], wherein a number average molecular weight is in the range of 500 to 10,000.

[7] A lubricant for a magnetic recording medium comprising the fluorine-containing ether compound described in any one of [1] to [6].

[8] A magnetic recording medium in which at least a magnetic layer, a protective layer, and a lubricant layer are sequentially provided on a substrate, wherein the lubricant layer contains the fluorine-containing ether compound according to any one of [1] to [6].

[9] The magnetic recording medium according to [8], wherein an average film thickness of the lubricant layer is 0.5 nm to 2 nm.

The fluorine-containing ether compound of the present invention is suitable to be used as a material for a lubricant for magnetic recording media.

Since the lubricant for magnetic recording media of the present invention contains the fluorine-containing ether compound of the present invention, a lubricant layer having excellent wear resistance can be formed even when the thickness is small.

Since the magnetic recording medium of the present invention has a lubricant layer having excellent wear resistance, the magnetic recording medium is excellent in reliability and durability.

BRIEF DESCRIPTION OF THE DRAWINGS

FIG. 1 is a schematic cross-sectional view showing an embodiment of a magnetic recording medium of the present invention.

DETAILED DESCRIPTION OF THE INVENTION

Hereinafter, the fluorine-containing ether compound, the lubricant for magnetic recording media (hereinafter sometimes referred to as "lubricant") and the magnetic recording medium of the present invention will be described in detail. This invention is not limited only to embodiments shown below.

[Fluorine-Containing Ether Compound]

The fluorine-containing ether compound of this embodiment is represented by the following formula (1).

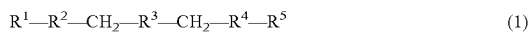

$$R^1-R^2-CH_2-R^3-CH_2-R^4-R^5 \quad (1)$$

In the formula (1), $R^3$ is a perfluoropolyether chain. $R^1$ is a terminal group bonded to $R^2$, and $R^5$ is a terminal group bonded to $R^4$. $R^1$ is an alkenyl group or an alkynyl group, and $R^5$ is a group containing a heterocyclic ring. $R^2$ is represented by the following formula (2), and $R^4$ is represented by the following formula (3). And, a in the formula (2) and b in the formula (3) are each independently an integer of 1 to 3.

[Chemical 2]

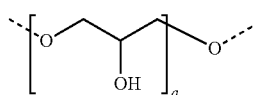

(2)

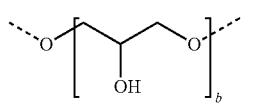

(3)

Here, the reason why excellent wear resistance can be obtained even when the thickness is small when the lubricant layer is formed on the protective layer of the magnetic recording medium using the lubricant containing the fluorine-containing ether compound of the present embodiment will be described.

The fluorine-containing ether compound of the present embodiment has a perfluoropolyether chain represented by $R^3$ (Hereinafter, it is sometimes abbreviated as "PFPE chain".) as shown in the formula (1). In the lubricant layer containing the fluorine-containing ether compound of the present embodiment, the PFPE chain covers the surface of the protective layer and imparts lubricity to the lubricant layer to reduce the frictional force between the magnetic head and the protective layer.

The fluorine-containing ether compound represented by the formula (1) is an asymmetric compound having different terminal groups ($R^1$, $R^5$). Specifically, the first terminal group ($R^1$) of the molecule is an alkenyl group or an alkynyl group, and the second terminal group ($R^5$) is a group containing a heterocyclic ring. Therefore, the fluorine-containing ether compound represented by the formula (1) has an excellent wear resistance compared with the compound having the same terminal groups bonded to both terminals, due to a synergistic effect of the terminal groups ($R^1$, $R^5$) which are bonded to both terminals, respectively, and have different functions.

In the fluorine-containing ether compound represented by the formula (1), $R^2$ is represented by the above formula (2), and $R^4$ is represented by the above formula (3).

Therefore, the fluorine-containing ether compound represented by the formula (1) contains at least one hydroxyl group in each of $R^2$ and $R^4$. In the lubricant layer containing the fluorine-containing ether compound of the present embodiment, the hydroxyl groups contained in $R^2$ and $R^4$ adheres the fluorine-containing ether compound with the protective layer, and as a result, wear resistance is improved. Therefore, it is presumed that the lubricant containing the fluorine-containing ether compound can form a lubricant layer having excellent wear resistance even when the thickness is reduced.

It is also presumed that in the lubricant layer containing the fluorine-containing ether compound of the present embodiment, an interaction (for example, hydrogen bonding) within the fluorine-containing ether compound is small, and an affinity between the protective layer and the terminal groups ($R^1$, $R^5$) and an affinity between the protective layer and the hydroxyl groups contained in $R^2$ and $R^4$ of the fluorine-containing ether compound are high. And as a result, good wear resistance can be obtained.

$R^2$ is a divalent linkage group and is represented by the above formula (2). In the formula (2), a is an integer of 1 to 3, which can be appropriately selected in accordance with the performance required for the lubricant containing the fluorine-containing ether compound. Preferably, a in the formula (2) is an integer of 1 to 2. When a in the formula (2) is 1 or more, the adhesion between the fluorine-containing ether compound and the protective layer can be improved in the lubricant layer containing the fluorine-containing ether compound. When a in the formula (2) is 3 or less, the polarity of the fluorine-containing ether compound is not excessively increased, and the occurrence of a pickup, in which the fluorine-containing ether compound adheres to the magnetic head as a foreign substance (smear), can be prevented.

$R^4$ is a divalent linkage group and is represented by the above formula (3). In the formula (3), b is an integer of 1 to 3, which can be appropriately selected in accordance with the performance required for a lubricant containing a fluorine-containing ether compound. In the formula (3), b is preferably an integer of 1 to 2. When b in the formula (3) is 1 or more, the adhesion between the fluorine-containing ether compound and the protective layer can be improved in the lubricant layer containing the fluorine-containing ether compound. When b in the formula (3) is 3 or less, the polarity of the fluorine-containing ether compound is not excessively increased, and the occurrence of a pickup, in which the fluorine-containing ether compound adheres to the magnetic head as a foreign substance (smear), can be prevented.

In the fluorine-containing ether compound of the present embodiment, the sum of the number of hydroxyl groups (—OH) in $R^2$ and the number of hydroxyl groups in $R^4$ is 2 or more, and preferably 3 or more. In the present embodiment, since each of $R^2$ and $R^4$ contains one or more hydroxyl groups, the adhesion between the fluorine-containing ether compound and the protective layer is improved in the lubricant layer containing the fluorine-containing ether compound. The sum of the number of hydroxyl groups contained in $R^2$ and the number of hydroxyl groups contained in $R^4$ is 6 or less, and preferably 4 or less. When the sum of the number of hydroxyl groups contained in $R^2$ and the number of hydroxyl groups contained in $R^4$ is 6 or less, the polarity of the fluorine-containing ether compound is not excessively increased, and the occurrence of a pickup, in which the fluorine-containing ether compound adheres to the magnetic head as a foreign substance (smear), can be prevented.

In the fluorine-containing ether compound represented by the formula (1), $R^2$ and $R^4$ may be the same or different.

In the fluorine-containing ether compound of the present embodiment represented by the formula (1), $R^1$ is a terminal group bonded to $R^2$, and $R^5$ is a terminal group bonded to $R^4$. $R^1$ and $R^5$ are different.

$R^1$ is an alkenyl group or an alkynyl group, and $R^5$ is a group containing a heterocyclic ring. Therefore, in the fluorine-containing ether compound represented by the formula (1), a synergistic effect between $R^1$ and $R^5$ is obtained. For example, when $R^1$ is an alkenyl group, a synergistic effect of a high affinity between the SP2 bond of the alkenyl group and the protective layer and another high affinity between the hetero atom of the group containing the heterocyclic ring and the protective layer are obtained. As a result, the fluorine-containing ether compound can form a lubricant layer having more excellent wear resistance.

In the fluorine-containing ether compound represented by the formula (1), $R^1$ is an alkenyl group or an alkynyl group. The alkenyl group or alkynyl group has a high affinity with the protective layer.

When $R^1$ is an alkenyl group, the double bond of the alkenyl group is preferably arranged at the farthest position from $R^2$. When $R^1$ is an alkenyl group, it is preferably an alkenyl group having 2 to 8 carbon atoms. Specifically, it is preferably at least one selected from the group consisting of an ethenyl group, an allyl group (propenyl group), a butenyl group, a pentenyl group, a hexenyl group, a heptenyl group and an octenyl group; and more preferably at least one selected from the group consisting of an allyl group, a butenyl group and a pentenyl group. When $R^1$ is an alkenyl group having 2 to 8 carbon atoms, the distance from the hydroxyl group contained in $R^2$ to the terminal atom of $R^1$ is suitable, and the lubricant layer including the compound exhibits good interaction with the protective layer.

When $R^1$ is an alkynyl group, the triple bond of the alkynyl group is preferably arranged at the farthest position from $R^2$. When $R^1$ is an alkynyl group, it is preferably an alkynyl group having 3 to 8 carbon atoms, more preferably at least one selected from the group consisting of a propynyl group ($CH_3$—C≡C—), a propargyl group (HC≡$CCH_2$—), a butynyl group, a methylbutynyl group, a pentynyl group, a methylpentynyl group, a hexynyl group, a heptynyl group and an octynyl group; and particularly preferably a propargyl group. When $R^1$ is an alkynyl group having 3 to 8 carbon atoms, the distance from the hydroxyl group contained in $R^2$ to the terminal atom of $R^1$ is suitable, and the lubricant layer containing the compound preferably exhibits good interaction with the protective layer.

When $R^1$ is at least one selected from the group consisting of an allyl group, a butenyl group, a pentenyl group and a propargyl group, the fluorine-containing ether compound can form a lubricant layer having more excellent wear resistance.

In the fluorine-containing ether compound represented by the formula (1), $R^5$ is a group containing a heterocyclic ring.

Examples of the groups containing the heterocyclic ring include pyrrolyl group, pyrazolyl group, methylpyrazolylmethyl group, imidazolyl group, furyl group, furfuryl group, oxazolyl group, isoxazolyl group, thienyl group, thienylethyl group, methylthiazolethyl group, thiazolyl group, methylthiazolylethyl group, isothiazolyl group, pyridyl group, pyrimidinyl group, pyridazinyl group, pyrazinyl group, indolinyl group, benzofuranyl group, benzothienyl group, benzoimidazolyl group, benzoxazolyl group, benzothiazolyl group, benzopyrazolyl group, benzoisoxazolyl group, benzoisothiazolyl group, quinolyl group, isoquinolyl group, quinazolinyl group, quinoxalinyl group, phthalazinyl group, and cinnolinyl group.

$R^5$ is preferably at least one selected from the group consisting of a group containing a thiophene ring, a group containing a thiazole ring, and a group containing a pyrazole ring. As the group containing a thiophene ring, a thienylethyl group is preferable. As the group containing a thiazole ring, a methylthiazolethyl group is preferable. And as the group containing a pyrazole ring, a methylpyrazolylmethyl group is preferable.

When $R^5$ is at least one selected from the group consisting of the group containing a thiophene ring, the group containing a thiazole ring, and the group containing a pyrazole ring, the fluorine-containing ether compound has high affinity with the protective layer and can form a lubricant layer having more excellent wear resistance.

The group containing a heterocyclic ring may have a substituent such as an alkyl group, an alkoxy group, a hydroxy group, a mercapto group, a carboxy group, a carbonyl group, an amino group, a cyano group, and the like.

In the fluorine-containing ether compound of the present embodiment represented by the formula (1), $R^3$ in the formula (1) is a perfluoropolyether chain (PFPE chain). $R^3$ is not particularly limited and can be appropriately selected in accordance with the performance required for the lubricant containing the fluorine-containing ether compound. Examples of the PFPE chains include chains obtained from a perfluoromethylene oxide polymer, a perfluoroethylene oxide polymer, a perfluoro-n-propylene oxide polymer, a perfluoroisopropylene oxide polymer, or a copolymer thereof.

Specifically, $R^3$ in the formula (1) is preferably represented by any one of the following formulae (4) to (6). There is no particular limitation on a sequence order of repeating units $(CF_2CF_2O)$ and $(CF_2O)$ in the formula (4). The formula (4) may contain any one of a random copolymer, a block copolymer, and an alternating copolymer obtained from monomer units $(CF_2-CF_2-O)$ and $(CF_2-O)$.

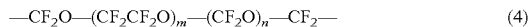

$$—CF_2O—(CF_2CF_2O)_m—(CF_2O)_n—CF_2— \quad (4)$$

In the formula (4), m and n represent the average degree of polymerization and each of them represents 0 to 30, and m or n is 0.1 or more.

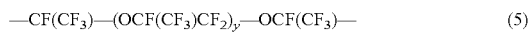

$$—CF(CF_3)—(OCF(CF_3)CF_2)_y—OCF(CF_3)— \quad (5)$$

In the formula (5), y represents the average degree of polymerization and represents 0.1 to 30.

$$—CF_2CF_2O—(CF_2CF_2CF_2O)_z—CF_2CF_2— \quad (6)$$

In the formula (6), z represents the average degree of polymerization and represents 0.1 to 30.

When y and z in the formulae (5) and (6) are each 0.1 to 30 (In the formula (4), each of m and n represents 0 to 30, and m or n is 0.1 or more.), the fluorine-containing ether compound provides a lubricant layer having good wear resistance. However, when each of m, n, y, and z exceeds 30, the viscosity of the fluorine-containing ether compound increases and it may be difficult to apply the lubricant containing the fluorine-containing ether compound. Therefore, m, n, y, and z are preferably 30 or less, and more preferably 20 or less.

When $R^3$ in the formula (1) is represented by any one of formulae (4) to (6), it is preferable because the synthesis of the fluorine-containing ether compound is easy. When $R^3$ is represented by the formula (4), it is more preferable because raw materials can be easily obtained.

When $R^3$ is represented by any one of formulae (4) to (6), the ratio of the number of oxygen atoms (number of ether bonds (—O—)) to the number of carbon atoms in the perfluoropolyether chain is proper. Therefore, the fluorine-containing ether compound having appropriate hardness is obtained. As a result, the fluorine-containing ether compound applied on the protective layer is less likely to aggregate on the protective layer, and a lubricant layer having a small thickness can be formed with a sufficient coverage rate. When $R^3$ is represented by any one of formulae (4) to (6), the fluorine-containing ether compound can provide a lubricant layer having good wear resistance.

Specifically, the fluorine-containing ether compound represented by the formula (1) is preferably any one of compounds represented by the following formulae (A) to (I). The repetition numbers m and n in the formulae (A) to (H) and the repetition number z in the formula (I) are values indicating an average value, and therefore m, n and z are not necessarily integers.

In the compounds represented by formulae (A) to (G) and (J), $R^1$ is an alkenyl group, $R^2$ is represented by the formula (2) in which a=1 or 2, $R^3$ is represented by the formula (4), $R^4$ is represented by the formula (3) in which b=1 or 2, and $R^5$ is a group containing a heterocyclic ring.

In the compound represented by the formula (H), $R^1$ is an alkynyl group, $R^2$ is represented by the formula (2) in which a=1, $R^3$ is represented by the formula (4), $R^4$ is represented by the formula (3) in which b=2, and $R^5$ is a group containing a heterocyclic ring.

In the compound represented by the formula (I), $R^1$ is an alkenyl group, $R^2$ is represented by the formula (2) in which a=2, $R^3$ is represented by the formula (6), $R^4$ is represented by the formula (3) in which b=2, and $R^5$ is a group containing a heterocyclic ring.

[Chemical 3]

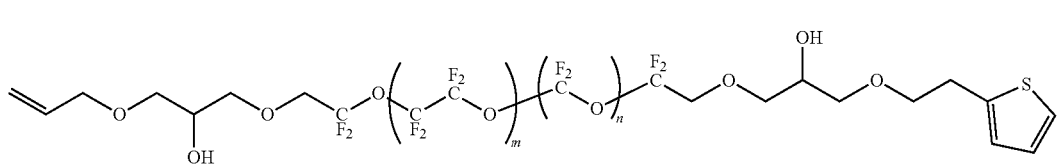

(A)

In the formula (A), m and n represent the average degree of polymerization, m represents 1 to 30, and n represents 0 to 30.

[Chemical 4]

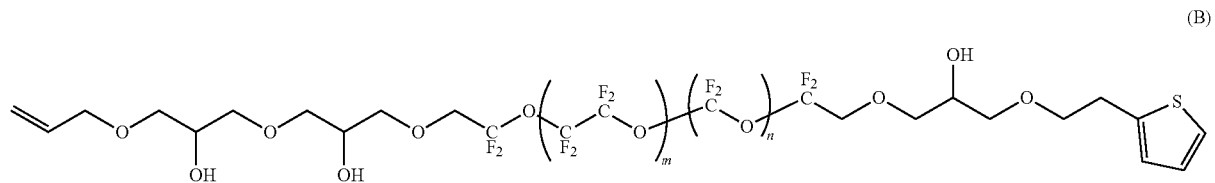

(B)

In the formula (B), m and n represent the average degree of polymerization, m represents 1 to 30, and n represents 0 to 30.

[Chemical 5]

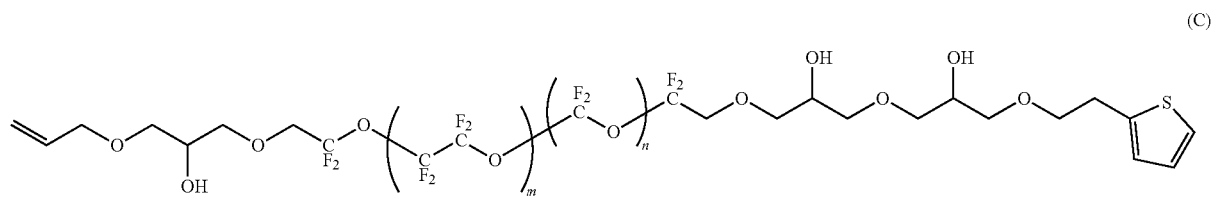

(C)

In the formula (C), m and n represent the average degree of polymerization, m represents 1 to 30, and n represents 0 to 30.

[Chemical 6]

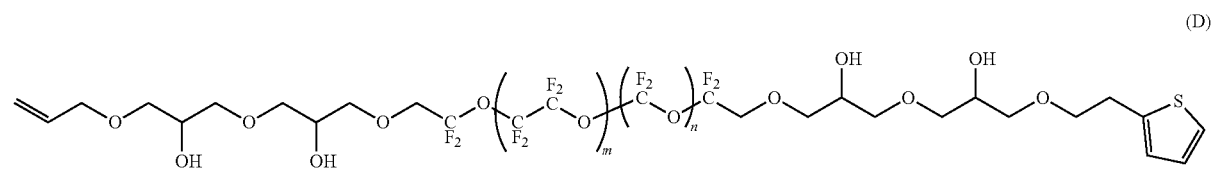

(D)

In the formula (D), m and n represent the average degree of polymerization, m represents 1 to 30, and n represents 0 to 30.

[Chemical 7]

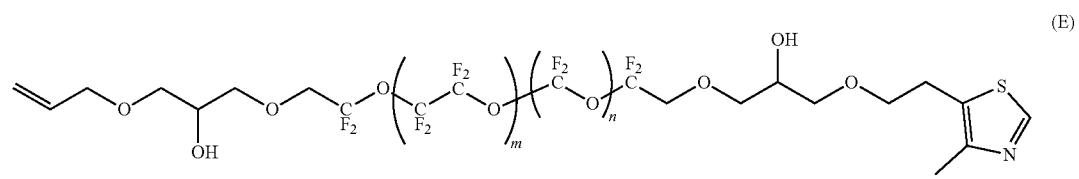

(E)

In the formula (E), m and n represent the average degree of polymerization, m represents 1 to 30, and n represents 0 to 30.

[Chemical 8]

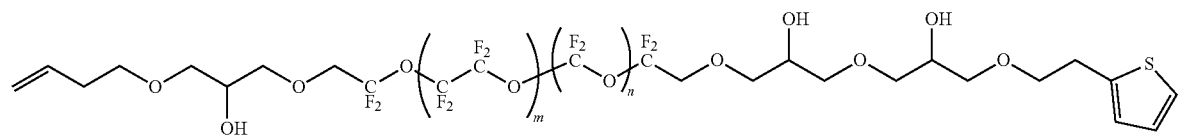

(F)

In the formula (F), m and n represent the average degree of polymerization, m represents 1 to 30, and n represents 0 to 30.

[Chemical 9]

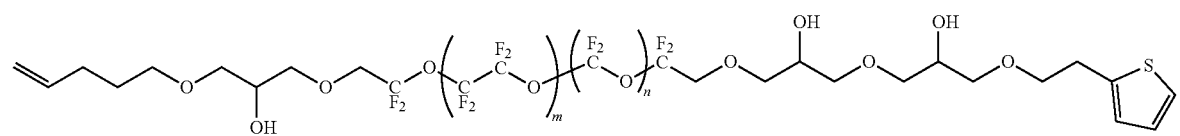

(G)

In the formula (G), m and n represent the average degree of polymerization, m represents 1 to 30, and n represents 0 to 30.

[Chemical 10]

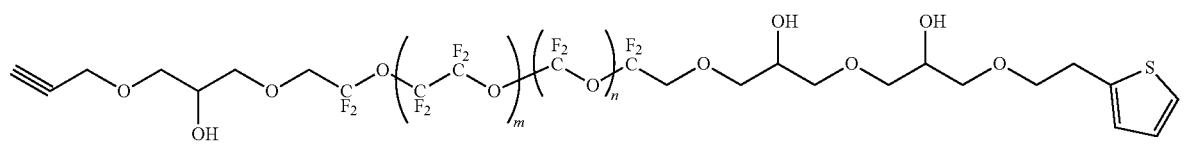

(H)

In the formula (H), m and n represent the average degree of polymerization, m represents 1 to 30, and n represents 0 to 30.

[Chemical 11]

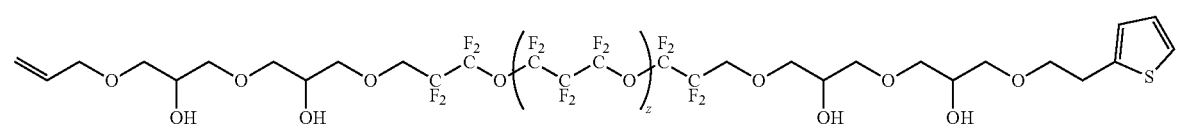

(I)

In the formula (I), z represents an average degree of polymerization and z represents 1 to 30.

[Chemical 12]

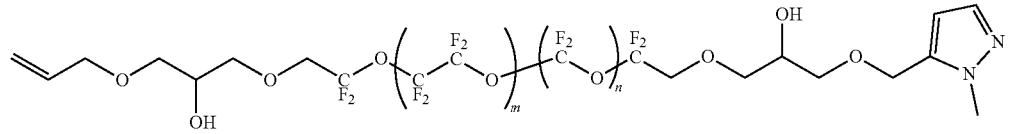

(J)

In the formula (J), m and n represent the average degree of polymerization, m represents 1 to 30, and n represents 0 to 30.

When the compound represented by the formula (1) is any one of compounds represented by the formulae (A) to (J), it is preferable because raw material is readily available and a lubricant layer having excellent wear resistance can be formed even when the thickness is small.

The fluorine-containing ether compound of the present embodiment preferably has a number average molecular weight (Mn) in the range of 500 to 10,000. When the number-average molecular weight is 500 or more, the lubricant containing the fluorine-containing ether compound of the present embodiment is less likely to evaporate, thereby preventing the lubricant from evaporating and transferring to the magnetic head. The number average molecular weight of the fluorine-containing ether compound is more preferably 1000 or more. Further, when the number average molecular weight is 10,000 or less, the viscosity of the fluorine-containing ether compound becomes appropriate, and a thin lubricant layer can be easily formed by applying the lubricant containing the fluorine-containing ether compound. The number average molecular weight of the fluorine-containing ether compound is more preferably 3000 or less because the viscosity of the lubricant using the fluorine-containing ether compound becomes easy to handle.

The number average molecular weight (Mn) of the fluorine-containing ether compound is a value measured by $^1$H-NMR and $^{19}$F-NMR by using AVANCE III 400 manufactured by Bruker Biospin. In NMR (nuclear magnetic resonance) measurements, the sample is diluted into a single solvent such as hexafluorobenzene, d-acetone, d-tetrahydrofuran, and the like; or a mixed solvent thereof, and the resulting sample is used for the measurement. The standard of $^{19}$F-NMR chemical shift was based on a hexafluorobenzene peak of −164.7 ppm, and the standard of $^1$H-NMR chemical shift was based on an acetone peak of 2.2 ppm.

"Production Method"

The method for producing the fluorine-containing ether compound according to the present embodiment is not particularly limited, and can be produced by using a conventionally known production method. The fluorine-containing ether compound of the present embodiment can be produced, for example, using the method shown below.

First, a fluorine-based compound in which hydroxymethyl groups (—CH$_2$OH) are arranged at both terminals of a perfluoropolyether chain corresponding to $R^3$ in the formula (1) is prepared.

Next, the hydroxyl group of the hydroxymethyl group arranged at one terminal of the fluorine-based compound is substituted with a group consisting of $R^1$—$R^2$— in the formula (1) (a first reaction). Then, the hydroxyl group of the hydroxymethyl group arranged at the other terminal is substituted with a terminal group consisting of —$R^4$—$R^5$ in the formula (1) (a second reaction).

The first reaction and the second reaction can be carried out by a conventionally known method, and can be appropriately determined according to the kind of $R^1$, $R^2$, $R^4$, and $R^5$ in the formula (1). Either of the first reaction or the second reaction may be performed firstly.

A compound represented by the formula (1) can be obtained by the above method.

In the present embodiment, it is preferable to use an epoxy compound in order to produce a fluorine-containing ether compound in which $R^2$ is represented by the formula (2) and $R^4$ is represented by the formula (3). The epoxy compound may be purchased commercially, or may be synthesized by using an alcohol having a structure corresponding to the terminal group represented by $R^1$ or $R^5$ of the fluorine-containing ether compound to be produced, and epichlorohydrin or epibromohydrin. Alternatively, the epoxy compound may be synthesized by oxidizing an unsaturated bond.

The fluorine-containing ether compound of the present embodiment is the compound represented by the formula (1). Therefore, when a lubricant layer is formed on the protective layer by using the lubricant containing the compound, the surface of the protective layer is covered by the PFPE chain represented by $R^3$ in the formula (1), and the frictional force between the magnetic head and the protective layer is reduced. Further, in the lubricant layer formed using the lubricant containing the fluorine-containing ether compound of the present embodiment, excellent wear resistance can be obtained by the intramolecular interaction between the terminal groups represented by $R^1$ and $R^5$ and one or more hydroxyl groups in each of $R^2$ and $R^4$, and/or the interaction between the terminal groups represented by $R^1$ and $R^5$ and the protective layer.

In the fluorine-containing ether compound of the present embodiment, the PFPE chain is adhered to the protective layer by the bonding between one or more hydroxyl groups in each of $R^2$ and $R^4$, which are linked to the PFPE chain, and the protective layer. Therefore, according to the fluorine-containing ether compound of the present embodiment, the lubricant layer and the protective layer are firmly bonded, and a lubricant layer having excellent wear resistance can be obtained.

[Lubricant for Magnetic Recording Media]

The lubricant for magnetic recording medium of this embodiment contains a fluorine-containing ether compound represented by the formula (1).

The lubricant of the present embodiment may use one or more known materials as a lubricant material by mixing them as necessary, as long as the known material does not impair the characteristics obtained by containing the fluorine-containing ether compound represented by the formula (1).

Specific examples of known materials include, for example, FOMBLIN (registered trademark) ZDIAC, FOMBLIN ZDEAL, FOMBLIN AM-2001 (the above materials are manufactured by Solvay Solexis), Moresco A20H (manufactured by Moresco) and the like. The known material used in combination with the lubricant of this embodiment preferably has a number average molecular weight of 1000 to 10,000.

When the lubricant of this embodiment contains materials other than the fluorine-containing ether compound represented by the formula (1), the amount of the fluorine-containing ether compound represented by the formula (1) in the lubricant of this embodiment is preferably 50% by mass or more, and more preferably 70% by mass or more.

Since the lubricant of this embodiment contains the fluorine-containing ether compound represented by the formula (1), the surface of the protective layer can be coated with a high coverage rate even when the thickness is reduced, and a lubricant layer having excellent adhesion to the protective layer can be formed. Therefore, according to the lubricant of the present embodiment, even when the thickness is small, a lubricant layer having excellent wear resistance can be obtained.

Further, since the lubricant of the present embodiment contains the fluorine-containing ether compound represented by the formula (1), the fluorine-containing ether compound in the lubricant layer present without adhering (adsorbing) to the protective layer is less likely to aggregate. Therefore, it is possible to prevent the fluorine-containing ether compound from aggregating and adhering to the magnetic head as a foreign substance (smear), thereby suppressing pickup.

Further, since the lubricant of the present embodiment contains the fluorine-containing ether compound represented by the formula (1), a lubricant layer having excellent wear resistance can be obtained by the intramolecular interaction between the terminal groups represented by $R^1$ and $R^5$ in the formula (1) and one or more hydroxyl groups in each of $R^2$ and $R^4$, and/or the interaction between the terminal groups and the protective layer.

[Magnetic Recording Medium]

The magnetic recording medium of the present embodiment is obtained by providing at least a magnetic layer, a protective layer, and a lubricant layer sequentially on a substrate.

In the magnetic recording medium of the present embodiment, one or more base layers can be provided between the substrate and the magnetic layer as necessary. Further, an adhesion layer and/or a soft magnetic layer can be provided between the base layer and the substrate.

FIG. 1 is a schematic cross-sectional view showing an embodiment of the magnetic recording medium of the present invention.

The magnetic recording medium 10 of this embodiment has a structure in which an adhesion layer 12, a soft magnetic layer 13, a first base layer 14, a second base layer 15, a magnetic layer 16, a protective layer 17 and a lubricant layer 18 are sequentially provided on a substrate 11.

"Substrate"

As the substrate 11, for example, a nonmagnetic substrate in which a film made of NiP or NiP alloy is formed on a base made of a metal or alloy material such as Al or Al alloy can be used.

As the substrate 11, a nonmagnetic substrate made of a nonmetallic material such as glass, ceramics, silicon, silicon carbide, carbon, or resin, or a nonmagnetic substrate obtained by forming a film made of NiP or NiP alloy on a base made of these nonmetallic materials, may be used.

"Adhesion Layer"

The adhesion layer 12 prevents the progress of corrosion of the substrate 11 that occurs when the substrate 11 and the soft magnetic layer 13 provided on the adhesion layer 12 are disposed in contact with each other.

The material of the adhesion layer 12 may be appropriately selected from, for example, Cr, Cr alloy, Ti, Ti alloy, CrTi, NiAl, AlRu alloy and the like. The adhesion layer 12 can be formed by, for example, a sputtering method.

"Soft Magnetic Layer"

The soft magnetic layer 13 preferably has a structure in which a first soft magnetic film, an intermediate layer made of a Ru film, and a second soft magnetic film are sequentially stacked. That is, it is preferable that the soft magnetic layer 13 has a structure in which the soft magnetic films above and below the intermediate layer are linked by antiferromagnetic coupling (AFC), by sandwiching the intermediate layer made of a Ru film between the two soft magnetic films.

Examples of the material of the first soft magnetic film and the second soft magnetic film include a CoZrTa alloy and a CoFe alloy.

It is preferable to add any one of Zr, Ta, and Nb to the CoFe alloy used for the first soft magnetic film and the second soft magnetic film. This promotes the amorphization of the first soft magnetic film and the second soft magnetic film, and as a result, it becomes possible to improve the orientation of the first base layer (seed layer) and reduce the flying height of the magnetic head.

The soft magnetic layer 13 can be formed by, for example, a sputtering method.

"First Base Layer"

The first base layer 14 is a layer for controlling the orientation and crystal sizes of the second base layer 15 and the magnetic layer 16 provided on top of the first base layer 14.

Examples of the first base layer 14 include a Cr layer, a Ta layer, a Ru layer, a CrMo alloy layer, a CoW alloy layer, a CrW alloy layer, a CrV alloy layer, and a CrTi alloy layer.

The first base layer 14 can be formed by, for example, a sputtering method.

"Second Base Layer"

The second base layer 15 is a layer for turning the magnetic layer 16 to a more favorable orientation. The second base layer 15 is preferably a layer made of Ru or a Ru alloy.

The second base layer 15 may be composed of a single layer or may be composed of a plurality of layers. When the second base layer 15 is composed of a plurality of layers, all the layers may be formed from the same material, or at least one layer may be formed from a different material.

The second base layer 15 can be formed by, for example, a sputtering method.

"Magnetic Layer"

The magnetic layer 16 is made of a magnetic film whose easy magnetization axis is oriented perpendicularly or horizontally to the substrate surface. The magnetic layer 16 is a layer containing Co and Pt, and may be a layer containing an oxide, Cr, B, Cu, Ta, Zr or the like in order to further improve the SNR characteristics.

Examples of the oxide contained in the magnetic layer 16 include $SiO_2$, SiO, $Cr_2O_3$, CoO, $Ta_2O_3$, and $TiO_2$.

The magnetic layer 16 may be composed of one layer, or may be composed of a plurality of magnetic layers made of materials having different compositions.

For example, when the magnetic layer 16 is composed of three layers of a first magnetic layer, a second magnetic layer, and a third magnetic layer that are stacked in order from the bottom, it is preferable that the first magnetic layer has a granular structure that includes a material containing Co, Cr, and Pt and further containing an oxide. As the oxide contained in the first magnetic layer, for example, an oxide of each Cr, Si, Ta, Al, Ti, Mg, and Co is preferably used. Among these, $TiO_2$, $Cr_2O_3$, $SiO_2$ or the like can be preferably used. The first magnetic layer is preferably made of a composite oxide in which two or more types of oxides are added. Of these, $Cr_2O_3$—$SiO_2$, $Cr_2O_3$—$TiO_2$, $SiO_2$—$TiO_2$ or the like can be preferably used.

The first magnetic layer may include at least one element selected from B, Ta, Mo, Cu, Nd, W, Nb, Sm, Tb, Ru, and Re in addition to Co, Cr, Pt, and oxide.

The same material as those used for the first magnetic layer can be used for the second magnetic layer. The second magnetic layer preferably has a granular structure.

The third magnetic layer preferably has a non-granular structure made of a material containing Co, Cr, Pt but containing no oxide. The third magnetic layer may contain one or more elements selected from B, Ta, Mo, Cu, Nd, W, Nb, Sm, Tb, Ru, Re, and Mn in addition to Co, Cr, and Pt.

When the magnetic layer 16 is formed of a plurality of magnetic layers, it is preferable to provide a nonmagnetic layer between adjacent magnetic layers. When the magnetic layer 16 is composed of three layers of the first magnetic layer, the second magnetic layer, and the third magnetic layer, it is preferable to provide a nonmagnetic layer between the first magnetic layer and the second magnetic layer, and between the second magnetic layer and the third magnetic layer.

Examples of materials that can be used favorably for the non-magnetic layers provided between the adjacent magnetic layers of the magnetic layer 16 include Ru, a Ru alloy, a CoCr alloy, a CoCrX1 alloy (wherein X1 represents one or more elements selected from among Pt, Ta, Zr, Re, Ru, Cu, Nb, Ni, Mn, Ge, Si, O, N, W, Mo, Ti, V and B), and the like.

It is preferable to use an alloy material containing an oxide, a metal nitride, or a metal carbide for the nonmagnetic layer provided between the adjacent magnetic layers of the magnetic layer 16. Specific examples of oxides that may be used include $SiO_2$, $Al_2O_3$, $Ta_2O_5$, $Cr_2O_3$, MgO, $Y_2O_3$, $TiO_2$, and the like. Examples of metal nitrides that may be used include AlN, $Si_3N_4$, TaN, CrN, and the like. Examples of metal carbides that may be used include TaC, BC, SiC, and the like.

The nonmagnetic layer can be formed by, for example, a sputtering method.

The magnetic layer 16 is preferably a magnetic layer for perpendicular magnetic recording in which the easy magnetization axis is oriented in a direction perpendicular to the substrate surface in order to achieve a higher recording density. The magnetic layer 16 may be in-plane magnetic recording.

The magnetic layer 16 may be formed by using any conventionally known method such as a vapor deposition method, an ion beam sputtering method, or a magnetron sputtering method. The magnetic layer 16 is usually formed by a sputtering method.

"Protective Layer"

The protective layer 17 protects the magnetic layer 16. The protective layer 17 may be composed of one layer or may be composed of a plurality of layers. Examples of the material of the protective layer 17 include carbon, nitrogen-containing carbon, silicon carbide, and the like.

As the protective layer 17, a carbon-based protective layer can be preferably used, and an amorphous carbon protective layer is particularly preferable. It is preferable that the protective layer 17 is a carbon-based protective layer because interaction with a polar group (particularly a hydroxy group) contained in the fluorine-containing ether compound in the lubricant layer 18 is further increased.

The adhesion between the carbon-based protective layer and the lubricant layer 18 can be controlled by making the carbon-based protective layer to contain hydrogenated carbon and/or nitrogenated carbon, and then adjusting the hydrogen content and/or the nitrogen content in the carbon-based protective layer. The hydrogen content in the carbon-based protective layer is preferably 3 to 20 atomic % as measured by the hydrogen forward scattering method (HFS). Further, the nitrogen content in the carbon-based protective layer is preferably 4 to 15 atomic % as measured by X-ray photoelectron spectroscopy (XPS).

The hydrogen and/or nitrogen contained in the carbon-based protective layer need not be uniformly contained in the entire carbon-based protective layer. For example, the carbon-based protective layer is preferably a composition gradient layer in which nitrogen is contained on the lubricant layer 18 side of the protective layer 17 and hydrogen is contained on the magnetic layer 16 side of the protective layer 17. In this case, the adhesion between the magnetic layer 16 and the carbon-based protective layer and the adhesion between the lubricant layer 18 and the carbon-based protective layer are further improved.

The film thickness of the protective layer 17 is preferably 1 nm to 7 nm. When the thickness of the protective layer 17 is 1 nm or more, the performance of the protective layer 17 is sufficiently obtained. The thickness of the protective layer 17 is preferably 7 nm or less from the viewpoint of reducing the thickness of the protective layer 17.

As a method for forming the protective layer 17, a sputtering method using a target material containing carbon, a chemical vapor deposition (CVD) method using a hydrocarbon raw material such as ethylene or toluene, an ion beam deposition (IBD) method, or the like can be used.

When a carbon-based protective layer is formed as the protective layer 17, it can be formed by, for example, a DC magnetron sputtering method. In particular, when a carbon-based protective layer is formed as the protective layer 17, it is preferable to form an amorphous carbon protective layer by plasma CVD. The amorphous carbon protective layer formed by the plasma CVD method has a uniform surface and small roughness.

"Lubricant Layer"

The lubricant layer 18 prevents contamination of the magnetic recording medium 10. Further, the lubricant layer 18 reduces the frictional force of the magnetic head of the magnetic recording/reproducing apparatus that slides on the magnetic recording medium 10, and improves the durability of the magnetic recording medium 10.

The lubricant layer 18 is formed on and is in contact with the protective layer 17, as shown in FIG. 1. The lubricant layer 18 includes the above-described fluorine-containing ether compound.

When the protective layer 17 disposed under the lubricant layer 18 is a carbon-based protective layer, the lubricant layer 18 is bonded to the protective layer 17 with a particularly high bonding strength. As a result, even when the lubricant layer 18 is thin, it is easy to obtain the magnetic recording medium 10 in which the surface of the protective layer 17 is coated with a high coverage rate, and contamination of the surface of the magnetic recording medium 10 can be effectively prevented.

The average film thickness of the lubricant layer 18 is preferably 0.5 nm (5 Å) to 2 nm (20 Å), more preferably 0.5 nm (5 Å) to 1 nm (10 Å). When the average film thickness of the lubricant layer 18 is 0.5 nm or more, the lubricant layer 18 is formed with a uniform film thickness without forming an island shape or a mesh shape. For this reason, the surface of the protective layer 17 can be covered with the lubricant layer 18 at a high coverage rate. Moreover, by making the average film thickness of the lubricant layer 18 to be 2 nm or less, the lubricant layer 18 can be made sufficiently thin, and the flying height of the magnetic head can be sufficiently reduced.

When the surface of the protective layer 17 is not coated with a sufficiently high coverage rate by the lubricant layer 18, an environmental substance adsorbed on the surface of the magnetic recording medium 10 passes through a gap of the lubricant layer 18 and enters below the lubricant layer 18. The environmental substances that enter the lower layer of the lubricant layer 18 are adsorbed and bonded with the protective layer 17 to form contaminants. Then, during magnetic recording/reproducing, the contaminant (aggregation component) adheres (transfers) to the magnetic head as a smear, and the magnetic head is damaged or the magnetic recording/reproducing characteristic of the magnetic recording/reproducing device is lowered.

Examples of the environmental substances that generate the contaminants include a siloxane compound (cyclic siloxane, linear siloxane), an ionic compound, a hydrocarbon having a relatively high molecular weight such as octacosane, and a plasticizer such as dioctyl phthalate. Examples of a metal ion contained in the ionic impurities include sodium ion, potassium ion, and the like. Examples of an inorganic ion contained in the ionic impurities include chlorine ion, bromine ion, nitrate ion, sulfate ion, ammonium ion, and the like. Examples of an organic ion contained in the ionic impurities include oxalate ion, formate ion, and the like.

"Method of Forming Lubricant Layer"

As a method of forming the lubricant layer 18, for example, a method of preparing a magnetic recording medium in the middle of production in which the layers up to the protective layer 17 are formed on the substrate 11, applying a solution for forming a lubricant layer on the protective layer 17, and then drying the layer, may be used.

The lubricant layer-forming solution can be obtained by dispersing and dissolving the lubricant for magnetic recording medium of the above-described embodiment in a solvent as necessary to obtain a viscosity and concentration suitable for the coating method.

Examples of solvents used in the lubricant layer-forming solution include fluorinated solvents such as Vertrel (registered trademark) XF (trade name, manufactured by Mitsui DuPont Fluorochemical Co., Ltd.).

The method for applying the lubricant layer-forming solution is not particularly limited, and examples thereof include a spin-coating method, a spray method, a paper coating method, and a dip method.

When using the dip method, for example, the following method can be used. First, the substrate 11 on which the layers up to the protective layer 17 are formed is dipped in the lubricant layer-forming solution placed in the dipping tank of the dip coater. Subsequently, the substrate 11 is pulled up from the dipping tank at a predetermined speed.

Thus, the lubricant layer-forming solution is applied to the surface of the protective layer 17 on the substrate 11.

By using the dip method, the lubricant layer-forming solution can be applied uniformly to the surface of the protective layer 17, and the lubricant layer 18 can be formed on the protective layer 17 with a uniform film thickness.

In this embodiment, it is preferable to heat the substrate 11 on which the lubricant layer 18 is formed. By performing the heat treatment, the adhesion between the lubricant layer 18 and the protective layer 17 is improved, and the adhesive strength between the lubricant layer 18 and the protective layer 17 is improved.

The heat treatment temperature is preferably 100 to 180° C. When the heat treatment temperature is 100° C. or higher, the effect of improving the adhesion between the lubricant layer 18 and the protective layer 17 is sufficiently obtained. Moreover, thermal decomposition of the lubricant layer 18 can be prevented by setting the heat treatment temperature to 180° C. or lower. The heat treatment time is preferably 10 to 120 minutes.

The magnetic recording medium 10 of the present embodiment is obtained by sequentially providing at least a magnetic layer 16, a protective layer 17, and a lubricant layer 18 on a substrate 11. In the magnetic recording medium 10 of the present embodiment, the lubricant layer 18 containing the above-mentioned fluorine-containing ether compound is formed on and in contact with the protective layer 17. The lubricant layer 18 coats the surface of the protective layer 17 with a high coverage rate even when the thickness is small.

Therefore, in the magnetic recording medium 10 of the present embodiment, environmental substances such as ionic impurities which generate contaminants are prevented from entering through the gaps of the lubricant layer 18. Therefore, the magnetic recording medium 10 of the present embodiment has a small amount of contaminants present on the surface. Further, the lubricant layer 18 in the magnetic recording medium 10 of the present embodiment is less likely to generate a foreign substance (smear), and can suppress pickup. The lubricant layer 18 in the magnetic recording medium 10 of the present embodiment has excellent wear resistance. Therefore, the magnetic recording medium 10 of the present embodiment has excellent reliability and durability.

EXAMPLE

Hereinafter, the present invention will be described in more detail below with reference to Examples and Comparative Examples. The present invention is not limited only to the following examples.

"Production of Lubricant"

Example 1

The compound represented by the above formula (A) was prepared by the following method.

In a 100 mL eggplant flask under a nitrogen gas atmosphere, 20.0 g of a compound (number average molecular weight 1000, molecular weight distribution 1.1) represented by $HOCH_2CF_2O(CF_2CF_2O)_q(CF_2O)_rCF_2CH_2OH$ (where q is 4.5 and r is 4.5.), 1.14 g of allyl glycidyl ether (molecular weight 114.14, 10 mmol) and 20 mL of t-butanol (t-BuOH) were charged and stirred at room temperature until they became uniform. To this homogeneous solution, 0.674 g (molecular weight 112.21, 6 mmol) of potassium tert-butoxide (t-BuOK) was added, and the reaction was carried out by stirring at 70° C. for 8 hours.

The resulting reaction product was cooled to 25° C., transferred to a separatory funnel containing 30 mL of water, and extracted 2 times with 80 mL of ethyl acetate. The organic layer was washed with water and dehydrated with anhydrous sodium sulfate. After the desiccant was filtered off, the filtrate was concentrated, and the residue was purified by silica gel column chromatography to obtain 8.91 g of a compound represented by the following formula (7) (molecular weight 1114, 8 mmol), as an intermediate.

[Chemical 13]

(7)

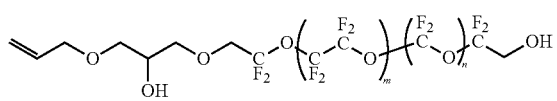

In the formula (7), m is 4.5 and n is 4.5.

In a 100 mL eggplant flask under a nitrogen gas atmosphere, 5.57 g (molecular weight 1114, 5.0 mmol) of the compound represented by the formula (7) which was obtained as an intermediate, 1.10 g (molecular weight 184.26, 6.0 mmol) of the compound represented by the following formula (8), and 50 mL of t-BuOH were charged and stirred at room temperature until they became uniform. To this homogeneous solution, 0.168 g of t-BuOK (molecular weight 112.21, 1.50 mmol) was added, and the reaction was carried out by stirring at 70° C. for 16 hours. The compound represented by the formula (8) was synthesized by using thiophene ethanol and epibromohydrin.

[Chemical 14]

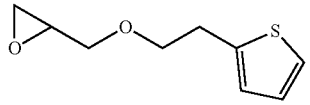

(8)

After the temperature of the reaction-terminated liquid returned to room temperature, the liquid was transferred to a separatory funnel containing 50 mL of water, and extracted 2 times with 100 mL of ethyl acetate. The organic layer was washed with water and dehydrated with anhydrous sodium sulfate. After the desiccant was filtered off, the filtrate was concentrated, and the residue was purified by silica gel column chromatography to obtain 3.88 g of Compound (A) (molecular weight 1295, 3.0 mmol). In the formula (A), m is 4.5 and n is 4.5.

$^1$H-NMR measurement of the obtained Compound (A) was performed, and the structure was identified from the following results.

Compound (A); $^1$H-NMR (CD$_3$COCD$_3$);

δ[ppm] 3.1 (2H), 3.5-4.2 (18H), 5.1-5.3 (2H), 5.9 (1H), 6.8-7.0 (2H), 7.2 (1H)

Example 2

The compound represented by the formula (B) was prepared by the following method.

In a 100 mL eggplant flask under a nitrogen gas atmosphere, 20.0 g of a compound (number average molecular weight 1000, molecular weight distribution 1.1) represented by HOCH$_2$CF$_2$O(CF$_2$CF$_2$O)$_q$(CF$_2$O)$_r$CF$_2$CH$_2$OH (where q is 4.5 and r is 4.5.), 2.72 g of a compound represented by the following formula (9) (molecular weight 272.34, 10 mmol), and 20 mL of t-BuOH were charged and stirred at room temperature until they became uniform. To this homogeneous solution, 0.674 g of t-BuOK (molecular weight 112.21, 6 mmol) was added, and the reaction was carried out by stirring at 70° C. for 8 hours. The compound represented by the formula (9) was synthesized, by oxidizing a compound obtained by protecting glycerol α,α'-diallyl ether using dihydropyran.

[Chemical 15]

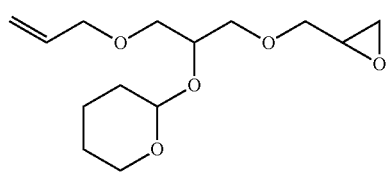

(9)

The resulting reaction product was cooled to 25° C., transferred to a separatory funnel containing 30 mL of water, and extracted 2 times with 80 mL of ethyl acetate. The organic layer was washed with water and dehydrated with anhydrous sodium sulfate. After the desiccant was filtered off, the filtrate was concentrated, and the residue was purified by silica gel column chromatography to obtain 10.15 g of a compound represented by the following formula (10) (molecular weight 1269, 8 mmol) as an intermediate.

[Chemical 16]

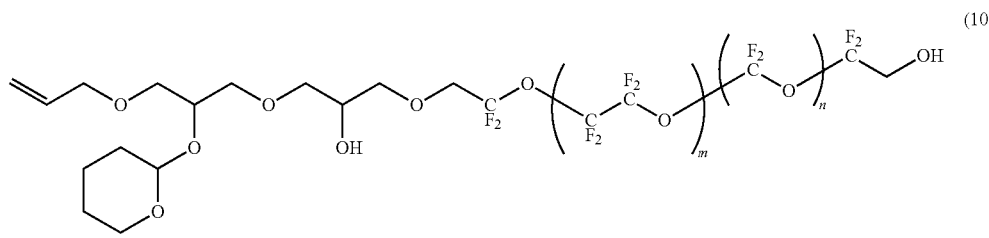

(10)

In the formula (10), m is 4.5 and n is 4.5.

In a 100 mL eggplant flask under a nitrogen gas atmosphere, 6.36 g of the compound represented by the formula (10) (molecular weight 1269, 5.0 mmol), 1.10 g of the compound represented by the formula (8) (molecular weight 184.26, 6.0 mmol), and 50 mL of t-BuOH were charged and stirred at room temperature until they became uniform. To this homogeneous solution, 0.168 g of t-BuOK (molecular weight 112.21, 1.50 mmol) was added, and the reaction was carried out by stirring at 70° C. for 16 hours.

After the temperature of the reaction liquid returned to room temperature, 20 g of 10% hydrogen chloride-methanol solution was added in the reaction liquid, and the mixture was stirred at room temperature for 4 hours. The reaction liquid was transferred little by little to a separatory funnel containing 70 mL of 8% aqueous sodium bicarbonate, and extracted 2 times with 200 mL of ethyl acetate. The organic layer was washed with water and 5% aqueous sodium bicarbonate and dehydrated with anhydrous sodium sulfate. After the desiccant was filtered off, the filtrate was concentrated, and the residue was purified by silica gel column chromatography to obtain 4.11 g of Compound (B) (molecular weight 1369, 3.0 mmol). In the formula (B), m is 4.5 and n is 4.5.

$^1$H-NMR measurement of the obtained Compound (B) was performed, and the structure was identified from the following results.

Compound (B); $^1$H-NMR (CD$_3$COCD$_3$);

δ[ppm] 3.1 (2H), 3.5-4.2 (23H), 5.1-5.3 (2H), 5.9 (1H), 6.8-7.0 (2H), 7.2 (1H)

Example 3

In a 100 mL eggplant flask under a nitrogen gas atmosphere, 6.35 g of a compound represented by the formula (7)

(molecular weight 1269, 5.0 mmol), 1.81 g of a compound represented by the following formula (11) (molecular weight 302.39, 6.0 mmol) and 50 mL of t-BuOH were charged and stirred at room temperature until they became uniform. To this homogeneous solution, 0.168 g of t-BuOK (molecular weight 112.21, 1.50 mmol) was added, and the reaction was carried out by stirring at 70° C. for 16 hours.

The compound represented by the formula (11) was synthesized by the following method. The compound represented by the formula (8) was hydrolyzed, and the primary hydroxyl group of the obtained compound was protected with a t-butyldimethylsilyl group. And then, the secondary hydroxyl group was protected with a methoxymethyl group, and the t-butyldimethylsilyl group was removed from the resulting compound. The compound represented by the formula (11) was synthesized by reacting the resulting primary hydroxyl group with epibromohydrin.

[Chemical 17]

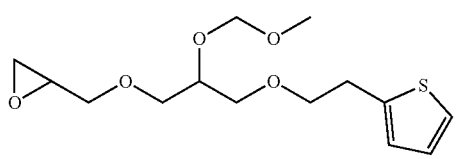

(11)

After the temperature of the reaction liquid returned to room temperature, the reaction liquid was transferred to a separatory funnel containing 50 mL of water, extracted two times with 100 mL of ethyl acetate, and the organic layer was concentrated. To this, 20 g of a 10% hydrogen chloride-methanol solution was added and the reaction liquid was stirred at room temperature for 1 hour. The reaction liquid was transferred little by little to a separatory funnel containing 70 mL of 8% aqueous sodium bicarbonate, and extracted two times with 200 mL of ethyl acetate. The organic layer was washed with water and dehydrated with anhydrous sodium sulfate. After the desiccant was filtered off, the filtrate was concentrated, and the residue was purified by silica gel column chromatography to obtain 4.11 g of Compound (C) (molecular weight 1369, 3.0 mmol). In the formula (C), m is 4.5 and n is 4.5.

$^1$H-NMR measurement of the obtained Compound (C) was performed, and the structure was identified from the following results.

Compound (C); $^1$H-NMR (CD$_3$COCD$_3$);

δ[ppm] 3.1 (2H), 3.5-4.2 (23H), 5.1-5.3 (2H), 5.9 (1H), 6.8-7.0 (2H), 7.2 (1H)

Example 4

4.33 g of Compound (D) (molecular weight 1443, 3 mmol) was obtained in the same manner as in Example 2, except that 1.81 g of a compound represented by the formula (11) (molecular weight 302.39, 6.0 mmol) was used instead of the compound represented by the formula (8). In the formula (D), m is 4.5 and n is 4.5.

$^1$H-NMR measurement of the obtained Compound (D) was performed, and the structure was identified from the following results.

Compound (D); $^1$H-NMR (CD$_3$COCD$_3$):

δ[ppm] 3.1 (2H), 3.5-4.2 (28H), 5.1-5.3 (2H), 5.9 (1H), 6.8-7.0 (2H), 7.2 (1H)

Example 5

3.93 g of Compound (E) (molecular weight 1310, 3.0 mmol) was obtained in the same manner as in Example 1, except that 1.20 g of a compound represented by the following formula (12) (molecular weight 199.27, 6 mmol) was used instead of the compound represented by the formula (8). The compound represented by the formula (12) was synthesized by using methylthiazole ethanol and epibromohydrin. In the formula (E), m is 4.5 and n is 4.5.

[Chemical 18]

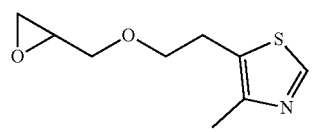

(12)

$^1$H-NMR measurement of the obtained Compound (E) was performed, and the structure was identified from the following results.

Compound (E); $^1$H-NMR (CD$_3$COCD$_3$);

δ[ppm] 2.35 (3H), 3.1 (2H), 3.5-4.2 (18H), 5.1-5.3 (2H), 5.9 (1H), 8.5 (1H)

Example 6

4.15 g of Compound (F) (molecular weight 1383, 3.0 mmol) was obtained in the same manner as in Example 3, except that 1.28 g of a compound (molecular weight 128.17, 10 mmol) represented by the following formula (13) was used instead of allyl glycidyl ether. The compound represented by the formula (13) was synthesized by using 3-butene-1-ol and epibromohydrin. In the formula (F), m is 4.5 and n is 4.5.

[Chemical 19]

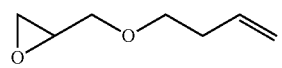

(13)

$^1$H-NMR measurement of the obtained Compound (F) was performed, and the structure was identified from the following results.

Compound (F); $^1$H-NMR (CD$_3$COCD$_3$);

δ[ppm] 2.2-2.4 (2H), 3.1 (2H), 3.5-4.3 (23H), 5.1-5.3 (2H), 5.9 (1H), 6.8-7.0 (2H), 7.2 (1H)

Example 7

4.19 g of Compound (G) (molecular weight 1397, 3 mmol) was obtained in the same manner as in Example 3, except that 1.42 g of a compound represented by the following formula (14) (molecular weight 142.20, 10 mmol) was used instead of allyl glycidyl ether. The compound represented by the formula (14) was synthesized by using 4-pentene-1-ol and epibromohydrin. In the formula (G), m is 4.5 and n is 4.5.

[Chemical 20]

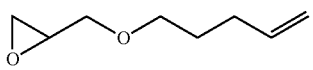
(14)

[superscript]1[/superscript]H-NMR measurement of the obtained Compound (G) was performed, and the structure was identified from the following results.
Compound (G); $^1$H-NMR (CD$_3$COCD$_3$);
δ[ppm] 1.6-1.8 (2H), 2.2-2.4 (2H), 3.1 (2H), 3.5-4.3 (23H), 5.1-5.3 (2H), 5.9 (1H), 6.8-7.0 (2H), 7.2 (1H)

Example 8

4.10 g of Compound (H) (molecular weight 1367, 3.0 mmol) was obtained in the same manner as in Example 3, except that 1.12 g of glycidyl propargyl ether (molecular weight 112.13, 10 mmol) was used instead of allyl glycidyl ether. In the formula (H), m is 4.5 and n is 4.5.
$^1$H-NMR measurement of the obtained Compound (H) was performed, and the structure was identified from the following results.
Compound (H); $^1$H-NMR (CD$_3$COCD$_3$);
δ[ppm] 2.5 (1H), 3.1 (2H), 3.5-4.2 (23H), 6.8-7.0 (2H), 7.2 (1H)

Example 9

4.41 g of Compound (I) (molecular weight 1471, 3.0 mmol) was obtained in the same manner as in Example 4, except that 20 g of a compound represented by HOCH$_2$CF$_2$CF$_2$O(CF$_2$CF$_2$CF$_2$O)CF$_2$CF$_2$CH$_2$OH (where s is 4.5) (number average molecular weight 1000, molecular weight distribution 1.1) was used instead of the compound represented by HOCH$_2$CF$_2$O(CF$_2$CF$_2$O)$_q$(CF$_2$O)$_r$CF$_2$CH$_2$OH (where q is 4.5 and r is 4.5.) (number average molecular weight 1000, molecular weight distribution 1.1). In the formula (I), z is 4.5.
$^1$H-NMR measurement of the obtained Compound (I) was performed, and the structure was identified from the following results.
Compound (I); $^1$H-NMR (CD$_3$COCD$_3$);
δ[ppm] 3.1 (2H), 3.5-4.2 (28H), 5.1-5.3 (2H), 5.9 (1H), 6.8-7.0 (2H), 7.2 (1H)

Example 10

3.84 g of Compound (J) (molecular weight 1279, 3.0 mmol) was obtained in the same manner as in Example 5, except that 1.01 g of a compound represented by the following formula (15) (molecular weight 168.19, 6 mmol) was used instead of the compound represented by the formula (12). The compound represented by the formula (15) was synthesized by using 1-methylpyrazole-5-methanol and epibromohydrin. In the formula (J), m is 4.5 and n is 4.5.

[Chemical 21]

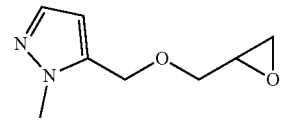
(15)

$^1$H-NMR measurement of the obtained Compound (J) was performed, and the structure was identified from the following results.
Compound (J); $^1$H-NMR (CD$_3$COCD$_3$);
δ[ppm] 3.5-4.3 (21H), 5.1-5.3 (2H), 5.9 (1H), 6.2 (1H), 7.3 (1H)

Comparative Example 1

A compound represented by the following formula (X) was synthesized by the method described in Patent Document 1.

[Chemical 22]

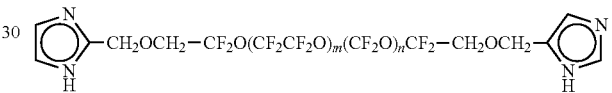
(X)

In the formula (X), m is 4.5 and n is 4.5.

Comparative Example 2

A compound represented by the following formula (Y) was synthesized by the method described in Patent Document 2.

[Chemical 23]

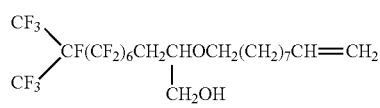
(Y)

The structures of R$^1$ to R$^5$ when the obtained compounds of Examples 1 to 10 are applied to the formula (1) are shown in Table 1. The number average molecular weights (Mn) of the compounds of Examples 1 to 10 were determined by $^1$H-NMR and $^{19}$F-NMR measurements described above. The results are shown in Table 1.

TABLE 1

| Example | R$^1$ | R$^2$ | R$^3$ | R$^4$ | R$^5$ | Mn |
|---|---|---|---|---|---|---|
| 1 | ≫⁀· | Formula (2) a = 1 | Formula (4) m = 4.5 n = 4.5 | Formula (3) b = 1 | 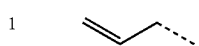 | 1295 |

TABLE 1-continued

| Example | R¹ | R² | R³ | R⁴ | R⁵ | Mn |
|---|---|---|---|---|---|---|
| 2 | (allyl) | Formula (2) a = 2 | Formula (4) m = 4.5 n = 4.5 | Formula (3) b = 1 | (thiophene-CH2CH2-) | 1369 |
| 3 | (allyl) | Formula (2) a = 1 | Formula (4) m = 4.5 n = 4.5 | Formula (3) b = 2 | (thiophene-CH2CH2-) | 1369 |
| 4 | (allyl) | Formula (2) a = 2 | Formula (4) m = 4.5 n = 4.5 | Formula (3) b = 2 | (thiophene-CH2CH2-) | 1443 |
| 5 | (allyl) | Formula (2) a = 1 | Formula (4) m = 4.5 n = 4.5 | Formula (3) b = 1 | (methylthiazole-CH2CH2-) | 1310 |
| 6 | (butenyl) | Formula (2) a = 1 | Formula (4) m = 4.5 n = 4.5 | Formula (3) b = 2 | (thiophene-CH2CH2-) | 1383 |
| 7 | (pentenyl) | Formula (2) a = 1 | Formula (4) m = 4.5 n = 4.5 | Formula (3) b = 2 | (thiophene-CH2CH2-) | 1397 |
| 8 | (propargyl) | Formula (2) a = 1 | Formula (4) m = 4.5 n = 4.5 | Formula (3) b = 2 | (thiophene-CH2CH2-) | 1367 |
| 9 | (allyl) | Formula (2) a = 2 | Formula (6) z = 4.5 | Formula (3) b = 2 | (thiophene-CH2CH2-) | 1471 |
| 10 | (allyl) | Formula (2) a = 1 | Formula (4) m = 4.5 n = 4.5 | Formula (3) b = 1 | (N-methylpyrazole-CH2-) | 1279 |

Next, a lubricant layer-forming solution was prepared by using the compounds obtained in Examples 1 to 10 and Comparative Examples 1 to 2 by the method described below. Then, using the obtained lubricant layer-forming solution, a lubricant layer of a magnetic recording medium was formed by the following method, and magnetic recording media of Examples 1 to 10 and Comparative Examples 1 to 2 were obtained.

"Lubricant Layer-Forming Solution"

The compounds obtained in Examples 1 to 10 and Comparative Examples 1 to 2 were each dissolved in Vertrel (registered trademark) XF (trade name, manufactured by Mitsui DuPont Fluoro Chemical Co., Ltd.), which is a fluorine-based solvent, and diluted with Vertrel so that the film thickness would be 9 Å to 10 Å when applied onto the protective layer, and a lubricant layer-forming solution was obtained.

"Magnetic Recording Media"

A magnetic recording medium in which an adhesion layer, a soft magnetic layer, a first base layer, a second base layer, a magnetic layer, and a protective layer were sequentially provided on a 65 mm diameter substrate was prepared. The protective layer was made of carbon.

The lubricant layer-forming solutions of Examples 1 to 10 and Comparative Examples 1 to 2 were applied by a dip method on the protective layer of the magnetic recording medium in which the layers up to the protective layer were formed. The dip method was performed at a dipping speed of 10 mm/sec, a dipping time of 30 sec, and a pulling speed of 1.2 mm/sec.

Thereafter, the magnetic recording medium coated with the lubricant layer-forming solution was placed in a thermostatic chamber at 120° C. and subjected to heat treatment for 10 minutes to remove the solvent in the lubricant layer-forming solution. As a result, a lubricant layer was formed on the protective layer to obtain a magnetic recording medium.

The film thicknesses of the lubricant layers of the obtained magnetic recording media of Examples 1 to 10 and Comparative Examples 1 to 2 were measured using FT-IR (trade name: Nicolet iS50, manufactured by Thermo Fisher Scientific). The results are shown in Table 2.

Next, wear resistance tests were performed on the magnetic recording media of Examples 1 to 10 and Comparative Examples 1 to 2 by the methods described below.

(Wear Resistance Test)

Using a pin-on-disk type friction and wear tester, an alumina ball having a diameter of 2 mm was used as a contact and was slid on the lubricant layer of the magnetic recording medium with a load of 40 gf at a sliding speed of 0.25 m/sec, to measure a coefficient of friction of the surface of the lubricant layer. The sliding time until the coefficient of friction sharply increases was measured on the surface of the lubricant layer. The sliding time until the coefficient of friction sharply increases was measured four times for the lubricant layer of each magnetic recording medium, and an average value (time) thereof was used as an indicator of the wear resistance of the lubricant coating film.

The results of the magnetic recording medium using the compounds of Examples 1 to 10 and the compounds of Comparative Examples 1 to 2 are shown in Table 2. The time until the coefficient of friction increases was evaluated as follows.

"AA": 650 sec or more
"BB": 550 sec or more and less than 650 sec
"CC": 450 sec or more and less than 550 sec
"DD": less than 450 sec The time until the coefficient of friction sharply increases can be used as an indicator of the wear resistance of the lubricant layer for the following reason. In the lubricant layer of the magnetic recording medium, wear progresses according to use of the magnetic recording medium. When the lubricant layer disappears due to wear, the contact and the protective layer are in direct contact with each other to cause the coefficient of friction to sharply increase. It is considered that the time until the coefficient of friction sharply increases has a correlation with the friction test.

TABLE 2

| | Compound | Film thickness (Å) | Time Until Coefficient of Friction Increases (sec) |
|---|---|---|---|
| Example 1 | A | 9.5 | AA |
| Example 2 | B | 9.5 | AA |
| Example 3 | C | 9.5 | AA |
| Example 4 | D | 9.5 | AA |
| Example 5 | E | 9.5 | AA |
| Example 6 | F | 9.5 | AA |
| Example 7 | G | 9.5 | AA |
| Example 8 | H | 9.5 | AA |
| Example 9 | I | 9.5 | AA |
| Example 10 | J | 9.5 | AA |
| Comparative example 1 | X | 9.5 | DD |
| Comparative example 2 | Y | 9.5 | DD |

As shown in Table 2, the magnetic recording media of Examples 1 to 10 had a longer sliding time until the coefficient of friction sharply increased and had better wear resistance than the magnetic recording media of Comparative Examples 1 and 2.

It is presumed that the results were achieved because in the magnetic recording media of Examples 1 to 10, $R^1$ in the compound represented by the formula (1) forming the lubricant layer is an alkenyl group or an alkynyl group, and $R^5$ is a group containing a heterocyclic ring.

INDUSTRIAL APPLICABILITY

By using the lubricant for a magnetic recording medium containing the fluorine-containing ether compound of the present invention, it is possible to form a lubricant layer capable of achieving excellent wear resistance even when the thickness is small.

DESCRIPTION/EXPLANATION OF REFERENCES

10 . . . Magnetic recording medium
11 . . . Substrate
12 . . . Adhesion layer
13 . . . Soft magnetic layer
14 . . . First base layer
15 . . . Second base layer
16 . . . Magnetic layer
17 . . . Protective layer
18 . . . Lubricant layer

The invention claimed is:

1. A fluorine-containing ether compound represented by the following formula (1),

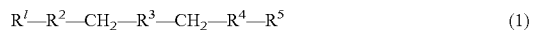

wherein, in the formula (1), $R^3$ is a perfluoropolyether chain; $R^1$ is a terminal group bonded to $R^2$; $R^5$ is a terminal group bonded to $R^4$; $R^1$ is an alkenyl group or an alkynyl group; $R^5$ is a group containing a heterocyclic ring; $R^2$ is represented by the following formula (2); $R^4$ is represented by the following formula (3); and a in the formula (2) and b in the formula (3) are each independently an integer of 1 to 3

[Chemical 1]

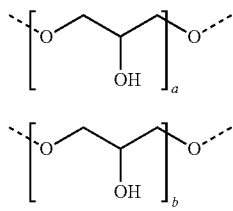

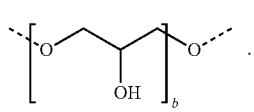

2. The fluorine-containing ether compound according to claim 1, wherein $R^1$ in the formula (1) is an alkenyl group having 2 to 8 carbon atoms or an alkynyl group having 3 to 8 carbon atoms.

3. The fluorine-containing ether compound according to claim 1, wherein $R^1$ in the formula (1) is at least one selected from the group consisting of an allyl group, a butenyl group, a pentenyl group and a propargyl group.

4. The fluorine-containing ether compound according to claim 1, wherein $R^5$ in the formula (1) is at least one selected from the group consisting of a group containing a thiophene ring, a group containing a thiazole ring, and a group containing a pyrazole ring.

5. The fluorine-containing ether compound according to claim 1, wherein $R^3$ in the formula (1) is any one of the following formulae (4) to (6),

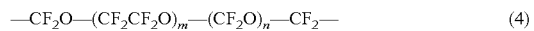

wherein, in the formula (4), m and n represent an average degree of polymerization and each of them represents 0 to 30, and m or n is 0.1 or more.

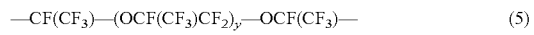

wherein, in the formula (5), y represents an average degree of polymerization and represents 0.1 to 30.

$$-CF_2CF_2O-(CF_2CF_2CF_2O)_z-CF_2CF_2- \quad (6)$$

wherein, in the formula (6), z represents an average degree of polymerization and represents 0.1 to 30.

6. The fluorine-containing ether compound according to claim 1, wherein a number average molecular weight is in the range of 500 to 10,000.

7. A lubricant for a magnetic recording medium comprising the fluorine-containing ether compound according to claim 1.

8. A magnetic recording medium in which at least a magnetic layer, a protective layer, and a lubricant layer are sequentially provided on a substrate, wherein the lubricant layer contains the fluorine-containing ether compound according to claim 1.

9. The magnetic recording medium according to claim 8, wherein an average film thickness of the lubricant layer is 0.5 nm to 2 nm.

10. The fluorine-containing ether compound according to claim 1, wherein the fluorine-containing ether compound is any one of compounds represented by the following formulae (A) to (J),

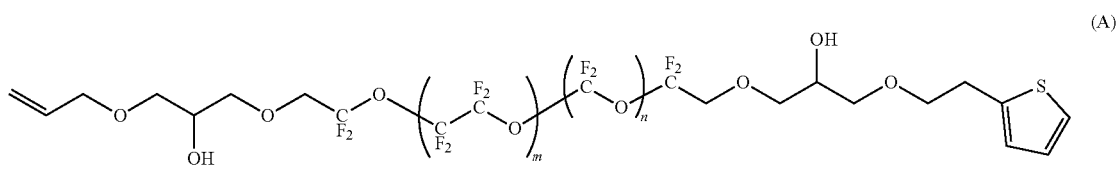

wherein, in the formula (A), m and n represent the average degree of polymerization, m represents 1 to 30, and n represents 0 to 30,

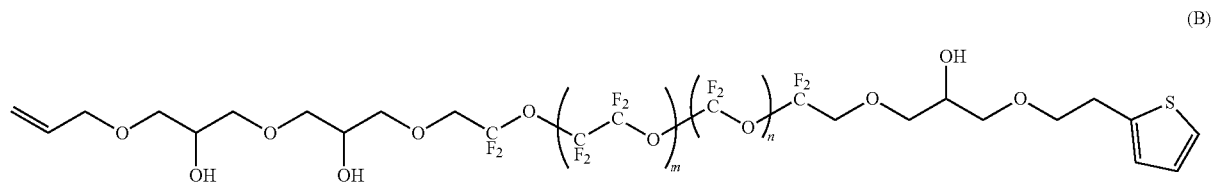

wherein, in the formula (B), m and n represent the average degree of polymerization, m represents 1 to 30, and n represents 0 to 30,

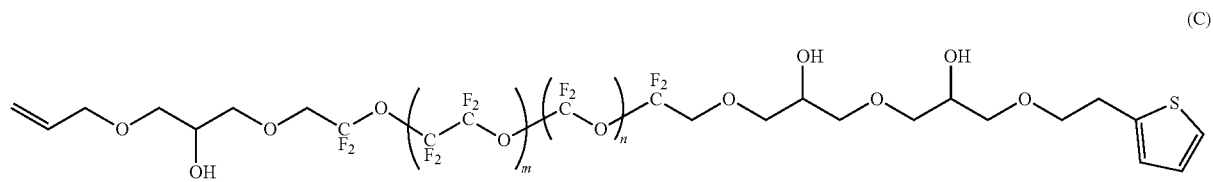

wherein, in the formula (C), m and n represent the average degree of polymerization, m represents 1 to 30, and n represents 0 to 30,

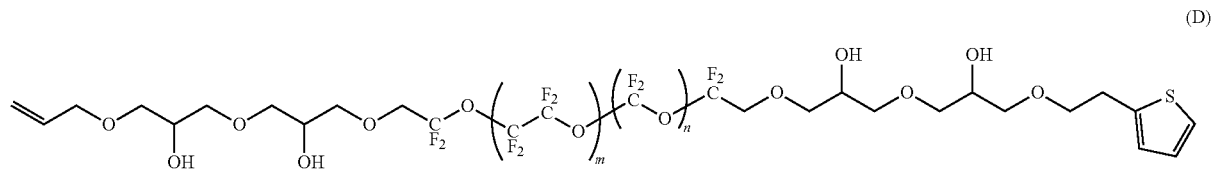

wherein, in the formula (D), m and n represent the average degree of polymerization, m represents 1 to 30, and n represents 0 to 30,

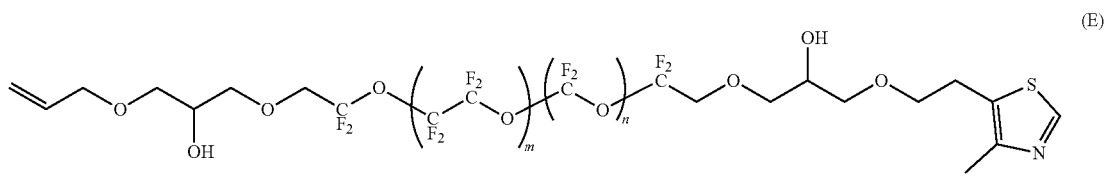

wherein, in the formula (E), m and n represent the average degree of polymerization, m represents 1 to 30, and n represents 0 to 30,

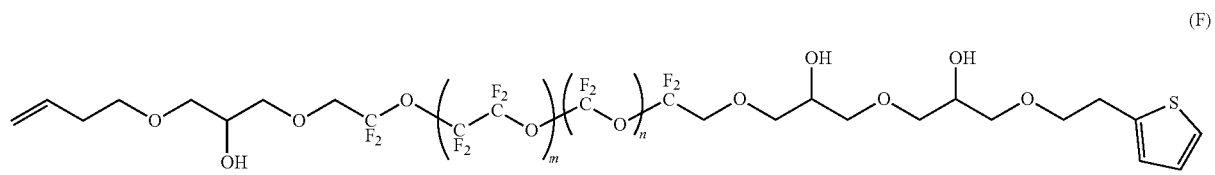

wherein, in the formula (F), m and n represent the average degree of polymerization, m represents 1 to 30, and n represents 0 to 30,

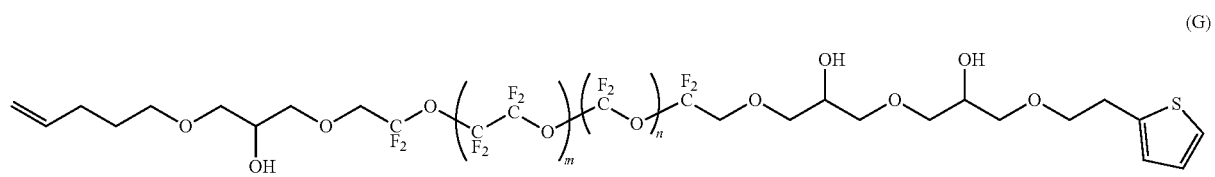

wherein, in the formula (G), m and n represent the average degree of polymerization, m represents 1 to 30, and n represents 0 to 30,

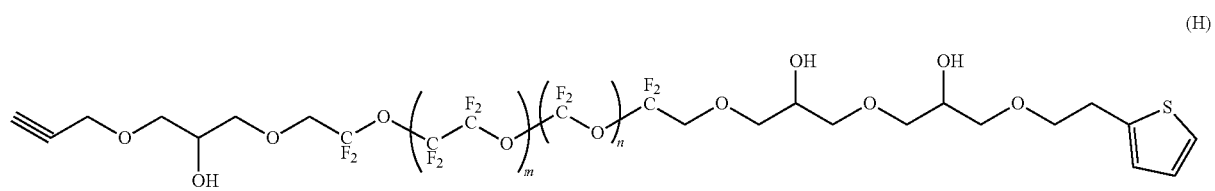

wherein, in the formula (H), m and n represent the average degree of polymerization, m represents 1 to 30, and n represents 0 to 30,

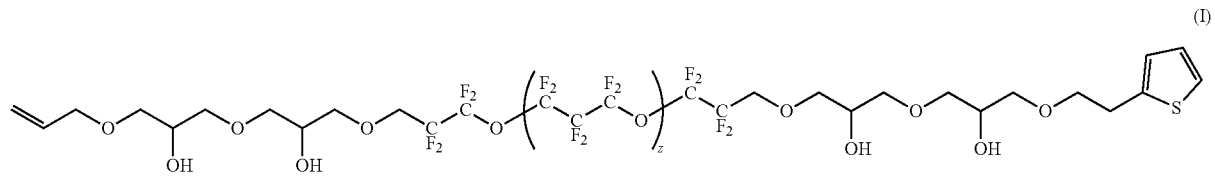

wherein, in the formula (I), z represents an average degree of polymerization and z represents 1 to 30, and
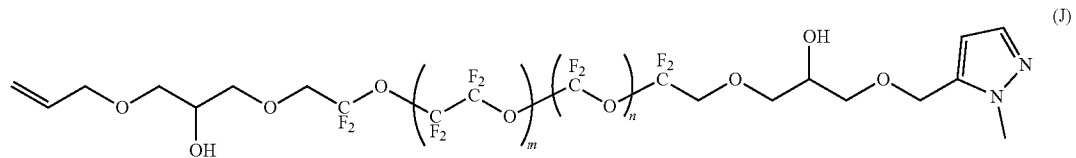
(J)
wherein, in the formula (J), m and n represent the average degree of polymerization, m represents 1 to 30, and n represents 0 to 30.
* * * * *